US010460050B2

(12) United States Patent
Tamaoki (10) Patent No.: US 10,460,050 B2
(45) Date of Patent: Oct. 29, 2019

(54) TOPOGRAPHY SIMULATION APPARATUS, TOPOGRAPHY SIMULATION METHOD, AND TOPOGRAPHY SIMULATION PROGRAM

(71) Applicant: TOSHIBA MEMORY CORPORATION, Minato-ku, Tokyo (JP)

(72) Inventor: Naoki Tamaoki, Tokyo (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 485 days.

(21) Appl. No.: 15/254,335

(22) Filed: Sep. 1, 2016

(65) Prior Publication Data

US 2017/0262556 A1 Sep. 14, 2017

(30) Foreign Application Priority Data

Mar. 10, 2016 (JP) ................................ 2016-047282

(51) Int. Cl.
*G06F 17/50* (2006.01)
*G16C 60/00* (2019.01)

(52) U.S. Cl.
CPC ...... *G06F 17/5009* (2013.01); *G06F 17/5018* (2013.01); *G16C 60/00* (2019.02)

(58) Field of Classification Search
CPC .................................................. G06F 17/5018
USPC .......................................................... 703/2
See application file for complete search history.

(56) References Cited

U.S. PATENT DOCUMENTS

| 5,070,469 | A | * | 12/1991 | Kunikiyo | ............ G06F 17/5018 |
| | | | | | 257/E21.233 |
| 5,416,729 | A | * | 5/1995 | Leon | .................. G06F 17/5018 |
| | | | | | 345/420 |
| 7,385,603 | B2 | * | 6/2008 | Piponi | ..................... G06T 13/20 |
| | | | | | 345/423 |
| 8,209,155 | B2 | | 6/2012 | Ichikawa et al. | |
| 8,831,916 | B2 | * | 9/2014 | McDaniel | ........... G06F 17/5009 |
| | | | | | 703/2 |

(Continued)

FOREIGN PATENT DOCUMENTS

JP 3388203 B2 3/2003

OTHER PUBLICATIONS

Husain Ali Al-Mohssen: "Chemical Vapor Deposition Models Using Direct Simulation Monte Carlo with Non-Linear Chemistry and Level Set Profile Evolution", Massachusetts Institute of Technology, http://web.mit.edu/husain/www/SMThesis/Final.pdf, Sep. 2003, pp. 1-69.

(Continued)

*Primary Examiner* — Andy Ho
(74) *Attorney, Agent, or Firm* — Foley & Lardner LLP (57) ABSTRACT

A topography simulation apparatus includes a processor and a memory connected to the processor. The memory stores instructions executable by the processor to set a function indicating a position relationship between a point in a calculation region and a material surface in the calculation region. The memory stores further instructions executable by the processor to determine whether or not a particle moving in the calculation region collides with the material surface, and update a value of the function, responsive to determining that the particle collides with the material surface.

18 Claims, 10 Drawing Sheets

(56) References Cited

U.S. PATENT DOCUMENTS 9,189,577 B2    11/2015    Kuboi et al.

OTHER PUBLICATIONS

Kokkoris et al.: "Simulation of SiO2 and Si feature etching for microelectronics and microelectromechanical systems fabrication: A Combined Simulator Coupling Modules of Surface Etching, Local Flux Calculation, and Profile Evolution", J. Vac. Sci. Technol. A 22(4), Jul./Aug. 2004, pp. 1896-1902.
Synopsys, Inc.: "Sentaurus TCAD Industry Standard Process and Device Simulators", www.synopsys.com, 2012, pp. 1-4.

\* cited by examiner

TOPOGRAPHY SIMULATION APPARATUS, TOPOGRAPHY SIMULATION METHOD, AND TOPOGRAPHY SIMULATION PROGRAM

CROSS-REFERENCE TO RELATED APPLICATION

This application claims the benefit of and priority to Japanese Patent Application No. 2016-047282, filed Mar. 10, 2016, the entire contents of which are incorporated herein by reference.

FIELD

Embodiments described herein relate generally to a topography simulation apparatus, a topography simulation method, and a topography simulation program.

BACKGROUND

When a material is processed by chemical vapor deposition (CVD), reactive ion etching (RIE), or the like, topography simulation for calculating a change (e.g., development over time) in the topography of the material can be performed in advance. In the topography simulation, long calculation time may be taken to process a plurality of surface segments constituting a surface of the material or to repeatedly calculate development over time. Improvements in such topography simulation method remain desired.

SUMMARY

In some embodiments according to one aspect, a topography simulation apparatus may include a processor and a memory connected to the processor. The memory may store instructions executable by the processor to set a function indicating a position relationship between a point in a calculation region and a material surface in the calculation region. The memory may store further instructions executable by the processor to determine whether or not a particle moving in the calculation region collides with the material surface, and update a value of the function, responsive to determining that the particle collides with the material surface.

In some embodiments according to another aspect, a non-transitory computer-readable storage medium may store instructions as a topography simulation program executable by a processor to set a function indicating a position relationship between a point in a calculation region and a material surface in the calculation region. The computer-readable storage medium may store further instructions executable by the processor to determine whether or not a particle moving in the calculation region collides with the material surface, and update a value of the function, responsive to determining that the particle collides with the material surface.

In some embodiments according to still another aspect, a topography simulation method may include setting a function indicating a position relationship between a point in a calculation region and a material surface in the calculation region. It may be determined that a particle moving in the calculation region collides with the material surface. A value of the function may be updated, responsive to determining that the particle collides with the material surface. A changed topography of the material surface may be output based on the updated value of the function.

Other aspects and embodiments of the disclosure are also encompassed. The foregoing summary and the following detailed description are not meant to restrict the disclosure to any particular embodiment but are merely meant to describe some embodiments of the disclosure.

DETAILED DESCRIPTION

When a material is processed by chemical vapor deposition (CVD), reactive ion etching (RIE), or the like, topography simulation for calculating a change (e.g., development over time) in the topography of the material can be performed in advance. In the topography simulation, for example, the material surface is divided into a plurality of surface segments, the flux of a particle reaching each surface segment and the movement speed of the local surface of the material may be calculated using a Radiosity method. However, long calculation time may be taken to calculate the flux and the surface movement speed for all of the surface segments without contradiction. That may be because the calculation time is increased in the order of the square of the number of surface segments.

On the other hand, a technique using a direct simulation Monte Carlo (DSMC) method for the flux calculation may be applied. In this technique, particles are flown to the calculation region, and flux is calculated from the model of the movement and interaction of the particles. In this case, the calculation time is proportional to the number of particles, and does not depend on the number of surface segments. If the interaction of particles is negligible, the calculation using the DSMC method can independently be performed for each particle, and is suitable for parallel calculation. However, even when using the DSMC method, the flux is repeatedly calculated for each unit time, for time development calculation of the topography of a material. As the number of calculations is increased by repeating time development, the calculation time may be increased.

An object of some embodiments is to provide a topography simulation apparatus, a topography simulation method, and a topography simulation program, which are capable of reducing the calculation time of topography simulation of calculating a change in the topography of a material.

According to some embodiments, a topography simulation apparatus includes a function setting unit that sets a function indicating a position relationship between a point in a calculation region and a surface of a material in the calculation region. The apparatus further includes a collision determination unit that determines whether or not a particle moving in the calculation region collides with the material surface. The apparatus further includes a function updating unit that updates a value of the function, if it is determined that the particle collides with the material surface.

Hereinafter, some embodiments will be described with reference to the drawings.

Figure 1:
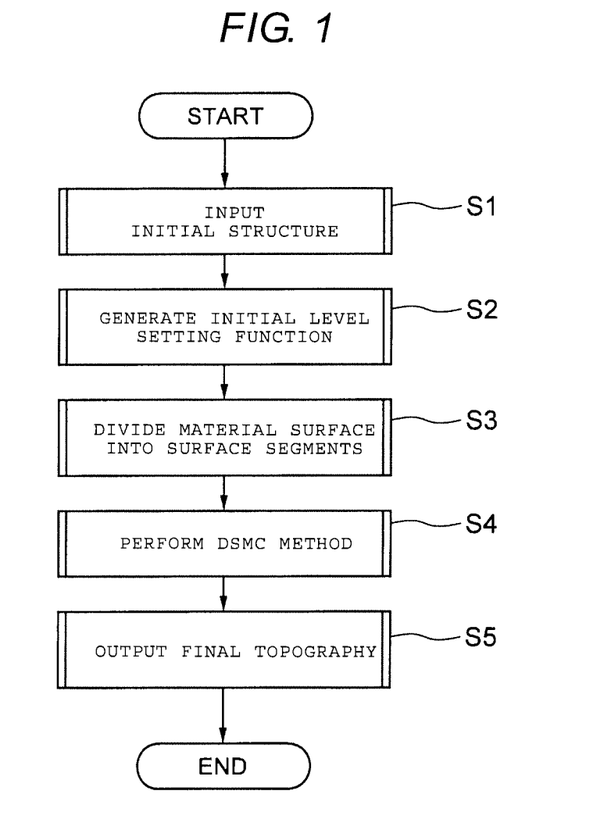
FIG. 1 is a flow chart illustrating a topography simulation method of some embodiments.

FIG. 1 is a flow chart illustrating a topography simulation method of some embodiments. The topography simulation method of some embodiments is performed using an information processing apparatus such as a personal computer or a workstation (see FIG. 15 and FIG. 16).

Figure 2:
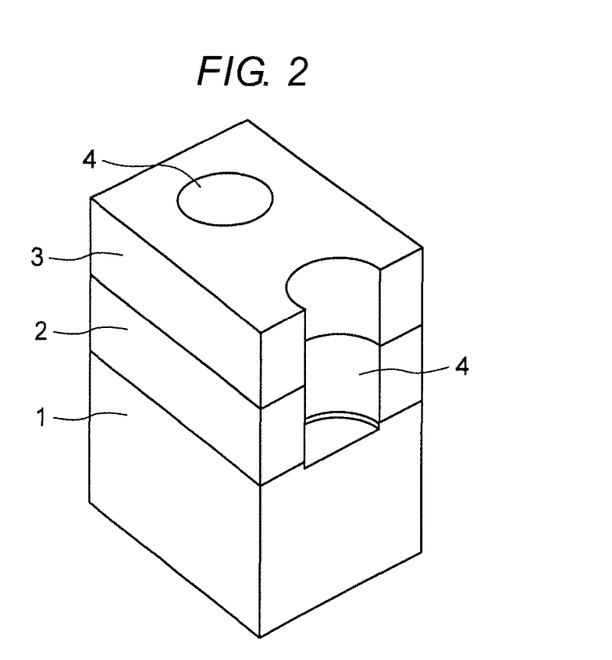
FIG. 2 is a perspective view illustrating an example of an initial structure of a material in some embodiments.

Referring to FIG. 1, first, an initial structure of material is input to the information processing apparatus (step S1). FIG. 2 is a perspective view illustrating an example of an initial structure of a material in some embodiments. The initial structure illustrated in FIG. 2 includes a substrate 1, a first layer 2 to be processed formed on the substrate 1, a second layer 3 to be processed formed on the first layer 2 to be processed, and an opening 4 passing through the first and second layer 2 and 3 to be processed. An example of the substrate 1 is a silicon substrate. An example of the first layer 2 to be processed is a silicon nitride film. An example of the second layer 3 to be processed is a silicon oxide film.

Figure 3:
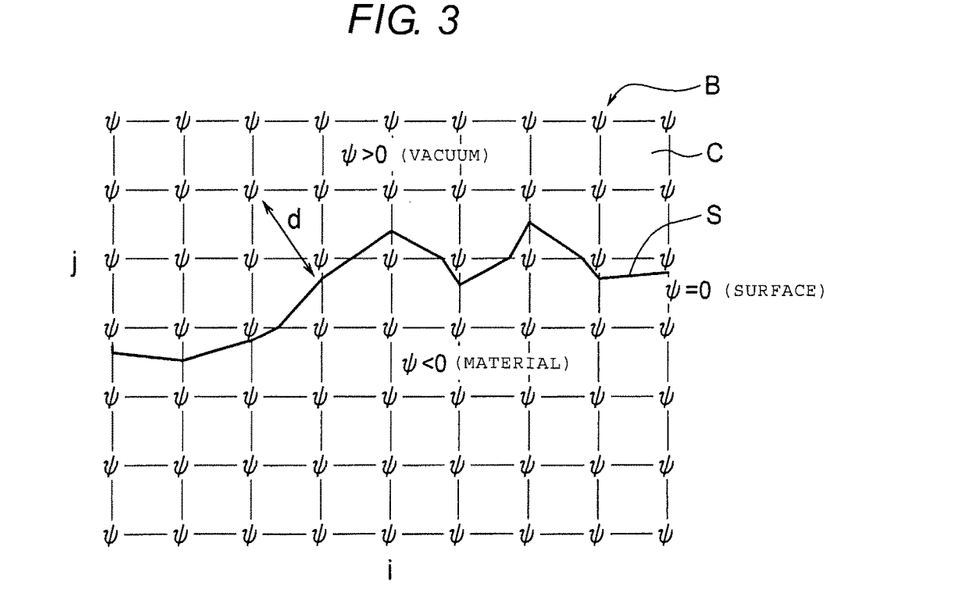
FIG. 3 is a schematic diagram illustrating a level set function.

Next, in some embodiments, an initial level set function is generated from the input initial structure (step S2). FIG. 3 is a schematic diagram illustrating a level set function. In FIG. 3, a level set function $\psi$ is illustrated in a calculation region (e.g., calculation space) of topography simulation. The calculation region illustrated in FIG. 3 includes a plurality of cells (e.g., meshes) C which are obtained by dividing the calculation region, and a plurality of lattice points (e.g., mesh points) B which are the vertices of these cells C. A reference symbol S indicates the material surface in the calculation region.

In some embodiment, the level set function $\psi$ is a function indicating a positional relationship between the lattice point and the material surface S. In some embodiments, the level set function $\psi$ is specified by a distance d between the lattice point and the material surface S, and has a value for each lattice point. In some embodiments, the value of the level set function $\psi$ is specified as 0 for the material surface S ($\psi=0$). In some embodiments, it is established that $\psi>0$ in the exterior of the material (e.g., in the vacuum) and $\psi<0$ in the interior of the material (e.g., within the material). In some embodiments, when generating the initial level set function, the position of the material surface S which is the closest to each lattice point is found, and the distance d between the lattice point and the found position is calculated. In some embodiments, if the lattice point is in the vacuum, the reference symbol of the initial level set function at the lattice point is set to a positive value. In some embodiments, if the lattice point is in the material, the reference symbol of the initial level set function in the lattice point is set to negative. In some embodiments, the initial level set function is not generated in step S2, but may be input to the information processing apparatus in step S1. In some embodiments, the function setting unit is configured to perform the process of steps S1 and S2.

Figure 4:
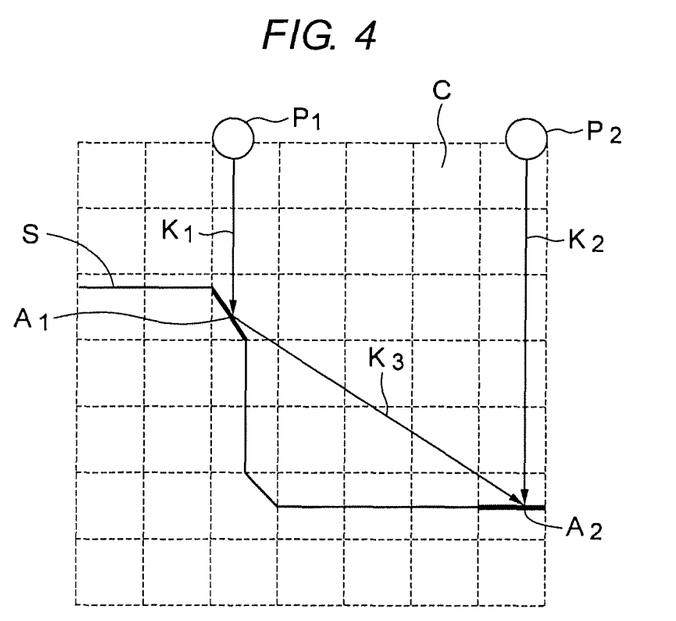
FIG. 4 is a schematic diagram illustrating a state where a material surface is divided into a plurality of surface segments.

Next, the material surface S is divided into a plurality of surface segments (step S3). FIG. 4 is a schematic diagram illustrating a state where the material surface S is divided into a plurality of surface segments. In FIG. 4, the material surface S is divided for each cell C so that the material surface S in a single cell C is a single surface segment. Reference symbols $A_1$ and $A_2$ indicate examples of the surface segment. In some embodiments, the calculation region (as illustrated in FIG. 4) is a two-dimensional region. In some embodiments, the calculation region may be a three-dimensional region. In some embodiments, the topography of each surface segment (as illustrated in FIG. 4) is a line segment. In some embodiments, the topography of each surface segment may be a point or a polygonal segment.

Referring to FIG. 4, reference symbols $P_1$ and $P_2$ are examples of particles (e.g., reactive species) that move in the calculation region. A reference symbol $K_1$ indicates the trajectory of a particle that directly reaches the surface segment $A_1$ from a gas layer. A reference symbol $K_2$ indicates the trajectory of a particle that directly reaches the surface segment $A_2$ from the gas layer. A reference symbol $K_3$ indicates the trajectory of a particle that indirectly reaches the surface segment $A_2$ from the gas layer through the surface segment $A_1$. In some embodiments, the particle movements indicated by the reference symbols $K_1$ and $K_2$ are taken into account when calculating the direct flux, and the particle movement indicated by the reference symbol $K_3$ is taken into account when calculating the indirect flux. The details of the particle movement in the calculation region will be described later.

Figure 15:
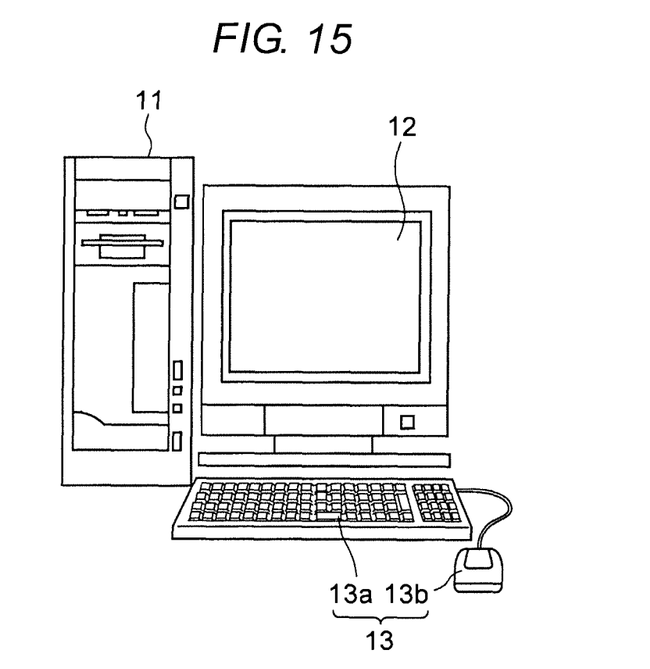
FIG. 15 is an external view illustrating a configuration of a topography simulation apparatus of some embodiments.
Figure 16:
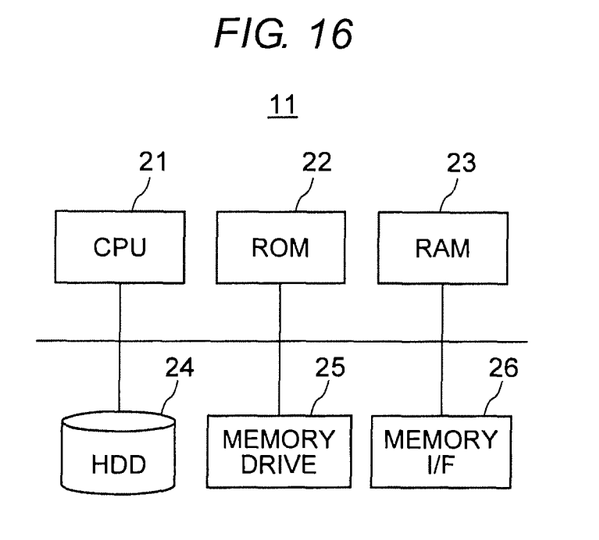
FIG. 16 is a block diagram illustrating a configuration of a control unit of FIG. 15.

Next, referring to FIG. 1, a change in the topography of the material is calculated by using a direct simulation Monte Carlo (DSMC) method (step S4) so that the final topography of the material is calculated. The details of step S4 will be described later. Thereafter, in some embodiments, the final topography of the material is output from the information processing apparatus (step S5), and the calculation is ended. In some embodiments, the final topography of the material can be output by the information processing apparatus (e.g., a device as shown in FIGS. 15 and 16) displaying it on a screen, storing it in a memory, or transmitting it to another device.

Figure 5:
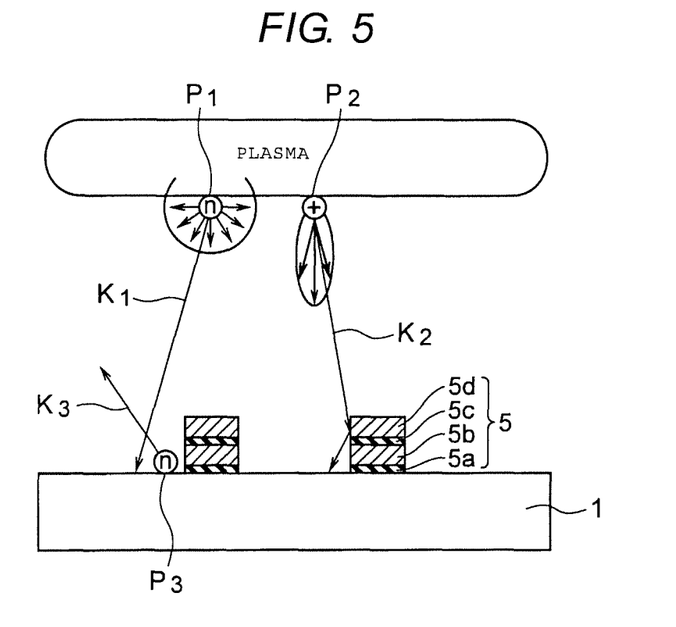
FIG. 5 is a cross-sectional view illustrating an example of a physical phenomenon handled in some embodiments.

FIG. 5 is a cross-sectional view illustrating an example of a physical phenomenon handled in some embodiments.

FIG. 5 illustrates a substrate 1, and cell transistors 5 formed on the substrate 1. Each cell transistor 5 includes a first insulating film 5a functioning as a gate insulating film, a first electrode layer 5b functioning as a floating gate, a second insulating film 5c functioning as an inter-gate insulating film, and a second electrode layer 5d functioning as a control gate. In some embodiments, the cell transistor 5 constitutes, for example, a NAND flash memory.

In some embodiments, as FIG. 5 illustrates, the substrate 1, the first insulating film 5a, the first electrode layer 5b, the second insulating film Sc, and the second electrode layer 5d (hereinafter, referred to as "layers to be processed") are processed by anisotropic etching using plasma. In FIG. 5, a reference symbol $P_1$ indicates neutral molecules that are activated by the plasma and are isotropically incident on the layer to be processed. A reference symbol $P_2$ indicates ions that are accelerated in a sheath region that forms an electric field gradient in the vicinity of the layer to be processed, and are anisotropically incident on layer to be processed. In some embodiments, the anisotropic etching is performed by a chemical reaction that the neutral molecules and ions cause in the surface of the layer to be processed.

In some embodiments, neutral molecules or ions flying to the vicinity of the layer to be processed may be incident on the surface of the layer to be processed, and may cause a reaction according to the materials or states of a local surface of the incident point. Examples of the reaction include an adsorption, reflection, desorption, deposition, etching, sputter, and the like. A reference symbol $K_1$ indicates an example of adsorption of the neutral molecule $P_1$. A reference symbol $K_2$ indicates an example of reflection of the ion $P_2$. A reference symbol $K_3$ indicates an example of desorption of a neutral molecule $P_3$. In some embodiments, if the neutral molecules and ions are re-emitted from the surface of the layer to be processed by the reflection or desorption, the neutral molecules and ions are incident on another surface to cause again the reaction. In some embodiments, the topography simulation can be performed by linking the transport (e.g., movement) of the neutral molecules and ions with a change in the surface topography due to the reaction.

Figure 6:
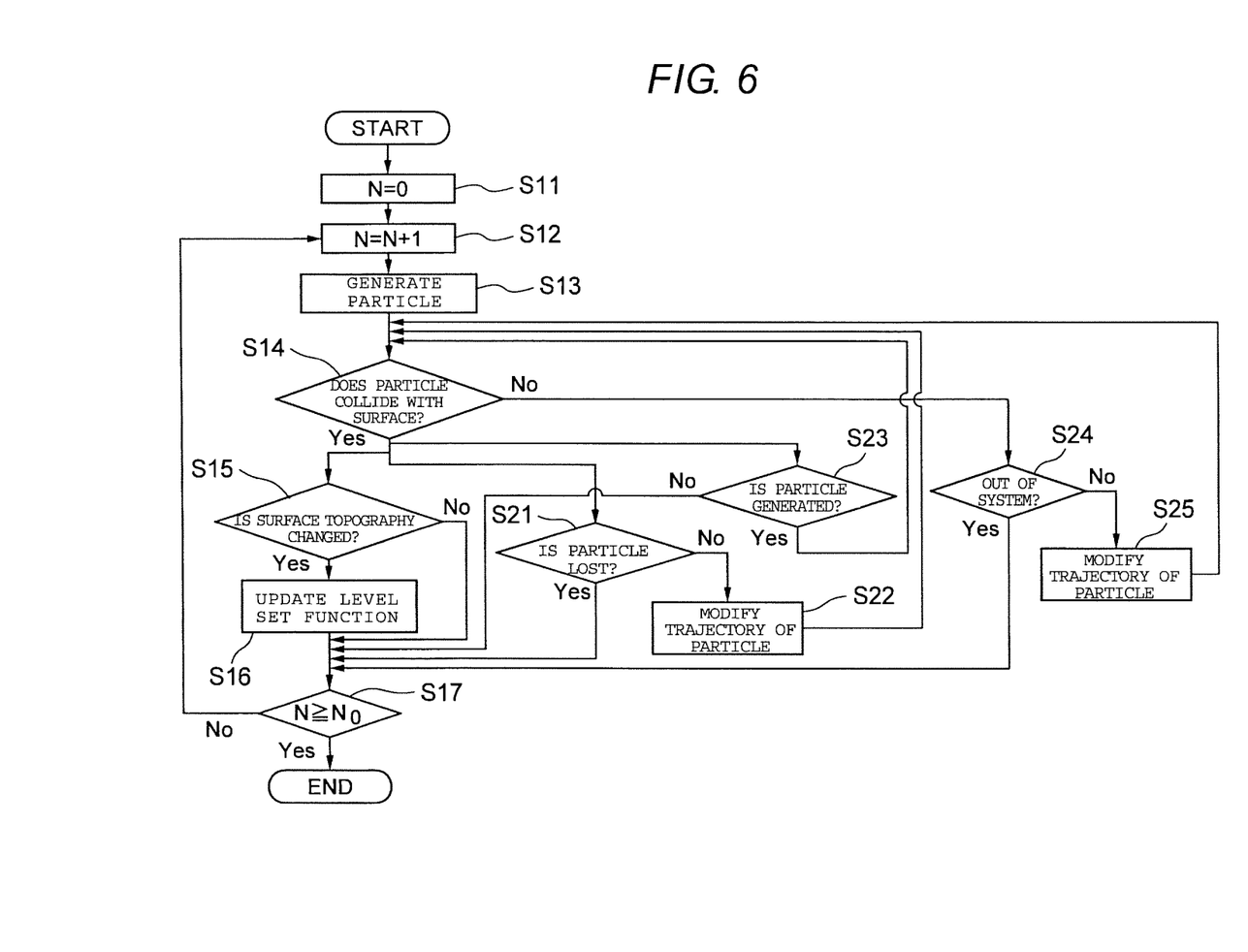
FIG. 6 is a flowchart illustrating the details of step S4 of FIG. 1.

FIG. 6 is a flowchart illustrating the details of step S4 of FIG. 1.

In some embodiments, a single particle simulating a molecule or an ion is flown to each calculation region at one time, and the trajectory of each particle is calculated by a DSMC method. In some embodiments, if the particle collides with the material surface, a change in the surface topography due to the collision is calculated.

Thus, referring to FIG. 6, in some embodiments, a variable N for distinguishing particles from each other is introduced, and the initial value of the variable N is set to 0 (step S11). Then, in some embodiments, each time the value of the variable N is increased by one, a single particle is generated in the calculation region (steps S12 and S13). In some embodiments, in step S14 and the subsequent processes, the trajectory of each particle is calculated.

In some embodiments, a time step Δt is set, and the movement of the particle between the time steps Δt and a change in the surface topography between the time steps Δt are alternately calculated. Meanwhile, in some embodiments, it is determined whether or not the particle flying to the calculation region collides with the material surface (step S14). In some embodiments, responsive to determining that the particle collides with the material surface, the change in the surface topography is calculated. In some embodiments, the collision determination unit is configured to perform the process of step S14.

In some embodiments, if the particle is determined to collide with the material surface, it is determined whether or not the topography of the material surface is changed due to the particle (step S15). For example, if the particle is a reactive species that is deposited in the local surface, or if the particle is reactive species that etches the local surface, the surface topography is determined to be changed. In some embodiments, the change determination unit is configured to perform the process of step S15.

In some embodiments, if the surface topography is determined to be changed due to the particle, the value of the level set function is updated (step S16). In some embodiments, the value of the level set function is changed from a value representing the surface topography before the topography change to a value representing the surface topography after the topography change. In some embodiments, the function updating unit is configured to perform the process of step S16. In this way, in some embodiments, if the particle is determined to collide with the material surface, and the surface topography is determined to be changed due to the particle, the value of the level set function is updated.

In some embodiments, if the particle is determined to collide with the material surface, it is also determined whether or not the particle is lost due to the collision (step S21). An example of the case of the particle being lost is adsorption. An example of the case of the particle not being lost is reflection. In some embodiments, if the particle is determined not to be lost, the trajectory of the particle is modified (step S22), and step S14 is executed again for the particle.

For example, if the particle is reflected at a probability W in the actual process, a random number of 0 to 1 may be generated in step S21. In some embodiments, if the value of the random number is 0 to W, the particle is not determined to be lost (e.g., the particle is reflected). In some embodiments, if the value of the random number is W to 1, the particle is determined to be lost (e.g., the particle is adsorbed). In some embodiments, if the particle is determined to be reflected, the reflection angle of the particle may be determined based on the incidence angle of the particle, or may randomly be determined by a random number.

In some embodiments, if the particle is determined to collide with the material surface, it is also determined whether or not a new particle is generated in the calculation region (step S23). An example of the case of a new particle being generated is desorption. In some embodiments, if a new particle is determined to be generated, step S14 is executed again for the particle.

In some embodiments, if the particle is not determined to collide with the material surface, it is also determined whether or not the particle moves out of the system (step S24). The details of the moving out of the system will be described later. In some embodiments, if the particle is not determined to move out of the system, the trajectory of the particle is modified (step S25), and step S14 is executed again for the particle. In some embodiments, if the particle is determined to move out of the system, the calculation of the particle is ended.

In some embodiments, the above process is repeatedly executed until the value of the variable N exceeds a predetermined value $N_0$ (step S17). The value $N_0$ represents the number of particles which are handled in the topography simulation of some embodiments. An example of the value $N_0$ is about one million. In some embodiments, if the value of the variable N exceeds the predetermined value $N_0$, step S4 is ended, and the final topography of the material is output in step S5 (see FIG. 1).

In addition, in some embodiments, the timing to end step S4 may be specified by a reference other than the value of the variable N. Examples of such reference include the thickness of the deposition process, the etching depth in the etching process, the processing times of various processes, or the like. In some embodiments, a plurality of references may be used, and step S4 may be ended when any reference is satisfied.

Figure 7A:
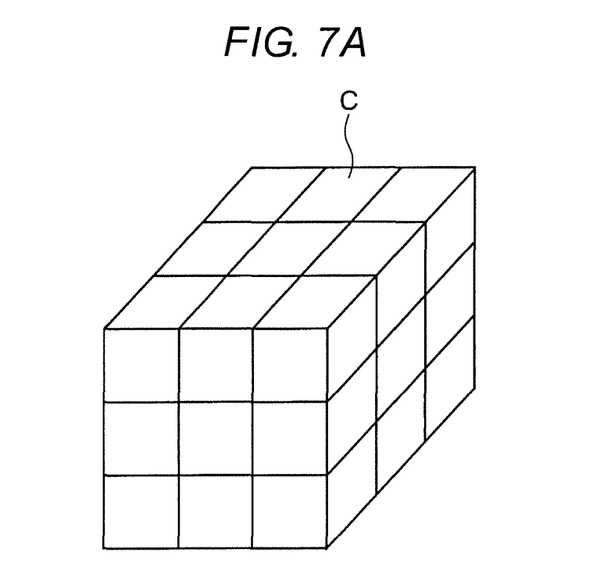
FIG. 7A and FIG. 7B are schematic diagrams illustrating a method of updating a level set function of some embodiments.
Figure 7B:
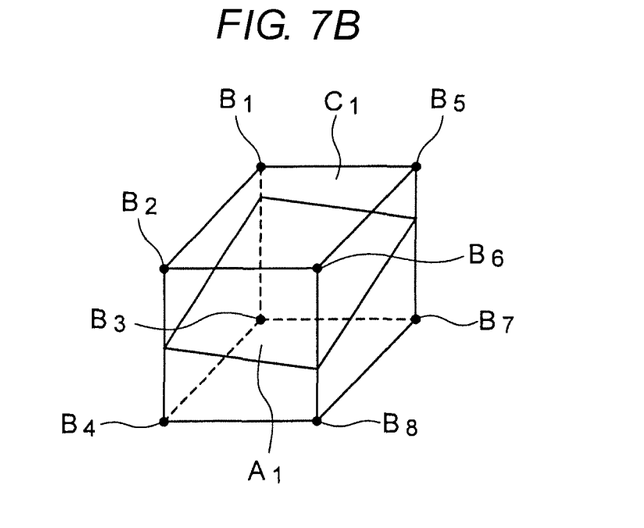

FIG. 7A and FIG. 7B are schematic diagrams illustrating a method of updating a level set function of some embodiments.

FIG. 7A depicts 27 pieces (3×3×3 pieces) of cells C in the calculation region. FIG. 7B depicts the cell $C_1$ in the center of FIG. 7A. The cell $C_1$ is adjacent to other 26 cells (e.g., some other cells among the other 26 cells) in FIG. 7A. FIG. 7B depicts a surface segment $A_1$ in the cell $C_1$, and lattice points $B_1$ to $B_8$ constituting the vertices of the cell $C_1$. The lattice points $B_1$ to $B_8$ are shared between the cell $C_1$ and some other cells among the other 26 cells C.

In some embodiments, in the above step S14, the cell C at the collision position of each particle is specified. The cell C is referred to as a collision cell. In some embodiments, when it is specified that the collision cell is the cell $C_1$, the values of the level set function of the lattice points $B_1$ to $B_8$ of the cell $C_1$ are selectively updated in step S16, among the values of the level set function. As a result, the topography of the surface segment in the 27 cells C in FIG. 7A is changed. In some embodiments, this is obtained by modeling the phenomenon in which the topography of the material surface is locally changed due to the collision of a single particle.

Figure 8:
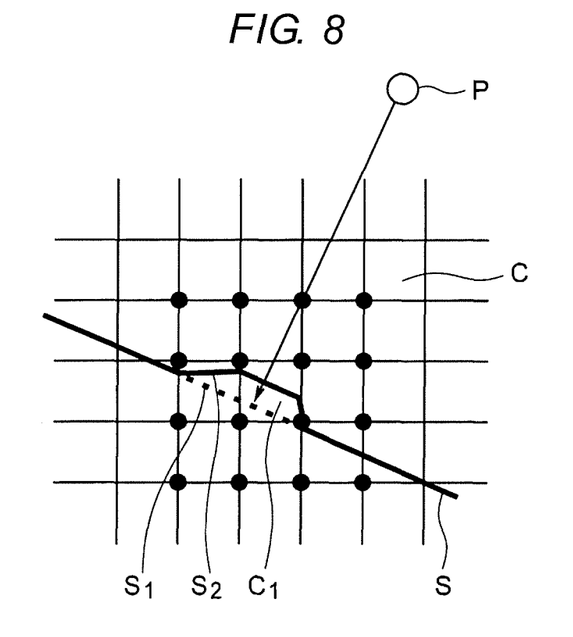
FIG. 8 is a schematic diagram illustrating the method of updating the level set function of some embodiments.

FIG. 8 is a schematic diagram illustrating the method of updating the level set function of some embodiments.

FIG. 8 depicts the cell $C_1$, and the particle P that collides with the cell $C_1$. FIG. 8 illustrates a state where the material surface S is changed from $S_1$ to $S_2$ due to collision of the particle P. It can be seen from FIG. 8 that the topography of the material surface S is locally changed.

Here, the simulated process of some embodiments and the actual process are compared.

In the actual process, a large number of particles are present at the same time in the space, and these particles cause the collision with the material surface and the change of the surface topography at the same time in parallel. Meanwhile, in some embodiments of the topography simulation, order numbers are given to a plurality of particles in the calculation region, and the effects of these particles on the materials are calculated separately.

In the actual process, the amount of change of the surface topography in each collision of a single particle depends on the density of the material. Meanwhile, in the process of some embodiments of the topography simulation, the amount of change of the surface topography in each collision of a single particle depends on the size of the cell C.

Therefore, in some embodiments, the change of the surface topography in each collision is not intended to simulate a change in the actual process, and corresponds to a virtual change. The reason is because a manner that the surface topography is changed in collision order in some embodiments does not correspond to the manner that the surface topography is changed in the order of time in the actual process. In some embodiments, a change in the surface topography obtained by the collision of a large number of particles corresponds to the change in the actual process, and a change in the surface topography during the calculation does not correspond to a change in the actual process.

The update of the level set function in some embodiments can be performed by the update routine of the level set function by a general level set method, except that the update of the level set function is locally performed. In some embodiments, the update is performed such that the level set function $\psi$ and the speed function F satisfy the following equation (1).

$$\psi_t + F|\nabla\psi| = 0 \tag{1}$$

However, $\nabla$ represents a vector differential operator, $|\nabla\psi|$ represents the norm of $\nabla\psi$, and $\psi_t$ represents the time partial differential of $\psi$. The speed function F represents the local surface moving speed of the material.

Figure 9A:
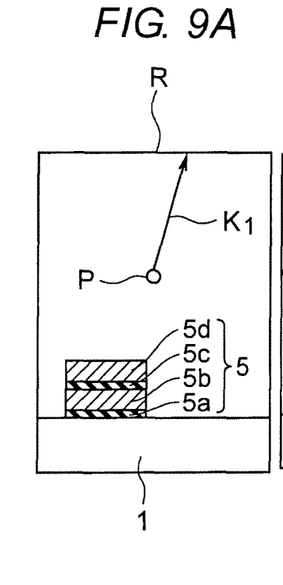
FIG. 9A, FIG. 9B and FIG. 9C are cross-sectional views illustrating an example of a boundary condition handled in some embodiments.
Figure 9B:
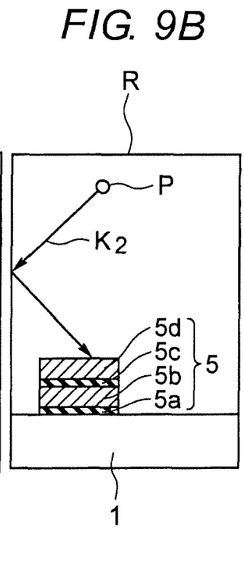
Figure 9C:
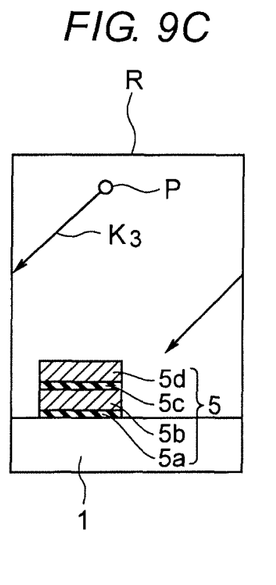

FIG. 9A, FIG. 9B and FIG. 9C are cross-sectional views illustrating an example of a boundary condition handled in some embodiments.

In some embodiments, when the particle is not determined to collide with the material surface, it is determined whether or not the particle moves out of the system (step S24 in FIG. 6). FIG. 9A illustrates the trajectory $K_1$ of the particle P that moves out of the system. In some embodiments, if the particle P reaches the upper end of the calculation region R, the particle P is determined to move out of the system. In this case, the calculation for particle P is ended.

Meanwhile, FIG. 9B and FIG. 9C illustrate the particle P that does not move out of the system. In some embodiments, if the particle P reaches the side end of the calculation region R, the particle P is not determined to move out of the system. In this case, the trajectory of the particle P is modified by boundary conditions (step S25 in FIG. 6). FIG. 9B illustrates the trajectory $K_2$ modified by mirror surface boundary conditions. FIG. 9C illustrates the trajectory $K_3$ modified by period boundary conditions. In some embodiments, any of the mirror surface boundary conditions and period boundary conditions may be employed.

As described above, in some embodiments, the final topography of the material is calculated by repeating the update of the level set function each time the particle collides with the material surface. In this case, the trajectory of the particle is calculated by the DSMC method. Therefore, according to some embodiments, it is possible to suppress the reduction of calculation speed and the increase of calculation time due to the increase in the number of surface segments, and to realize high-speed topography simulation. Further, according to some embodiments, faster topography simulation allows the reduction of the computation cost.

In addition, in some embodiments, the update of the level set function is performed for each collision of a particle, rather than for each time step. Therefore, according to some embodiments, it is possible to suppress reduction of calculation speed and an increase of calculation time caused by function update for each time step, and to realize high-speed topography simulation. For example, according to some embodiments, because the convergence of the particle flux distribution and the calculation of deformation of the material topography can be performed at the same time in parallel, there is no need to wait for the convergence of the particle flux distribution for each time step, and the time development calculation of the topography of the material can be faster.

In some embodiments, a function other than the level set function may be used, and the function value of a point other than the lattice point for the level set function may be used. In some embodiments, a level set method having a stable topography representation and high topography accuracy may be used. In some embodiments, the direction vector of the local surface is determined with high accuracy, because when considering the interaction between, for example, an ion and a material surface, the reaction speed is significantly increased depending on the incident angle of the ion. In some embodiments, in the level set method, it is possible to calculate the surface vector from the slope of the level set function with high accuracy and computational efficiency. Therefore, in the topography simulation of some embodiments, the level set method can be applied.

Figure 10:
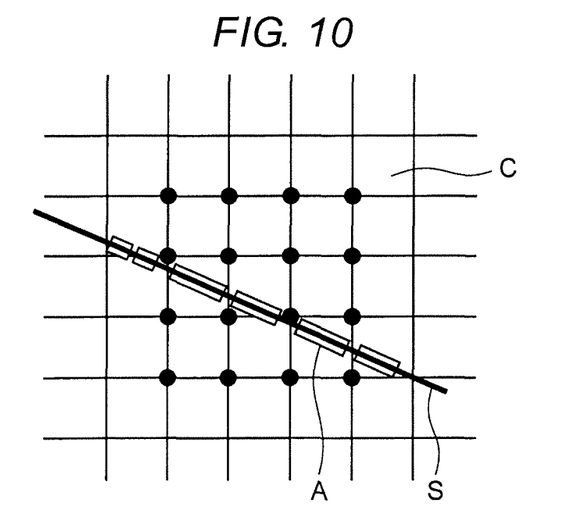
FIG. 10 is a schematic diagram illustrating a topography simulation method of some embodiments.

FIG. 10 is a schematic diagram illustrating a topography simulation method of some embodiments.

FIG. 10 illustrates a state in which the material surface S is divided into a plurality of surface segments A. In FIG. 10, the material surface S is divided for each cell C so that the material surface S in a single cell C is a single surface segment A.

In some embodiments, when calculating a deposition amount of a deposited film in deposition reaction simulation, the deposition amount depends on the size of the particle involved in the deposition reaction, and the density of the deposited film. Therefore, in some embodiments, if the same type of particles P1 and P2 are incident on the material surface, the deposition amount of the particle P1 and the deposition amount of the particle P2 are the same. Therefore, in some embodiments, if the same type of particles P1 and P2 are incident on the material surface by the deposition reaction, the value of the level set function is updated such that the amount of volume increase of the material due to the particle P1 and the amount of volume increase of the material due to the particle P2 are the same, in step S16 of FIG. 6.

This is also applied to the etching reaction. In some embodiments, if the same type of particles P1 and P2 are incident on the material surface by the etching reaction, the value of the level set function is updated such that the amount of volume decrease of the material due to the particle P1 and the amount of volume decrease of the material due to the particle P2 are the same, in step S16 of FIG. 6.

However, when dealing with the volume increase and the volume decrease of the material, as illustrated in FIG. 10, an area of the surface segment A may not be constant. For example, if the particle P1 collides with a small surface segment A at the deposition reaction, the amount of movement of the surface segment A is increased. In contrast, if the particle P2 collides with a large surface segment A at the deposition reaction, the amount of movement of the surface segment A is reduced. Therefore, in some embodiments, the value of the level set function is updated such that the amount of volume increase of the material due to the particle P1 and the amount of volume increase of the material due to the particle P2 are the same. In some embodiments, the amount of volume increase is determined by the product of the area of the surface segment A and the amount of movement of the surface segment A.

In this way, in some embodiments, the amount of movement of the surface segment A is changed depending on the position of the surface segment A such that the amount of volume change per particle is the same. As a result, in some embodiments, when simulating a situation in which a plurality of particles are uniformly incident on a flat material surface S, a simulation result is obtained in which unevenness occurs on the material surface S. Meanwhile, when actually performing the process of inputting uniformly the plurality of particles on the flat material surface S, unevenness typically does not occur on the material surface S. For example, the material surface S rises uniformly in the actual deposition reaction. Further, the material surface S is gradually uniformly lowered in the actual etching reaction. Therefore, when the amount of volume change of each particle is the same, the simulation result may not correspond to the actual result.

Therefore, in some embodiments, the value of the level set function is updated such that the surface movement distance of the material is constant every time the particle collides, when performing step S16 described above. In some embodiments, when a single particle collides with the material surface S, the value of the level set function is updated such that the surface movement distance due to the collision is a value of $F|\nabla\psi|$ in Equation (1). Therefore, according to some embodiments, it is possible to approximate the result of topography simulation to the actual result.

Here, the embodiment illustrated in FIG. 10 is compared with general topography simulation.

In the general topography simulation, the speed function F is handled when calculating the flux of material surface S. The speed function F corresponds to a deposition rate or an etching rate. On the other hand, in some embodiments, in the topography simulation by the DSMC method, after flying a large number of particles and simulating a collision, the flux of the material surface S is then calculated. Therefore, in some embodiments, the flux in each collision is not calculated, and the deposition amount and the etching amount by the flux of each collision are not determined. However, in some embodiments, since the value of the level set function of each collision is updated by using $F|\nabla\psi|$, it is possible to realize topography simulation with a high accuracy, as in the case of using a flux.

Figure 11:
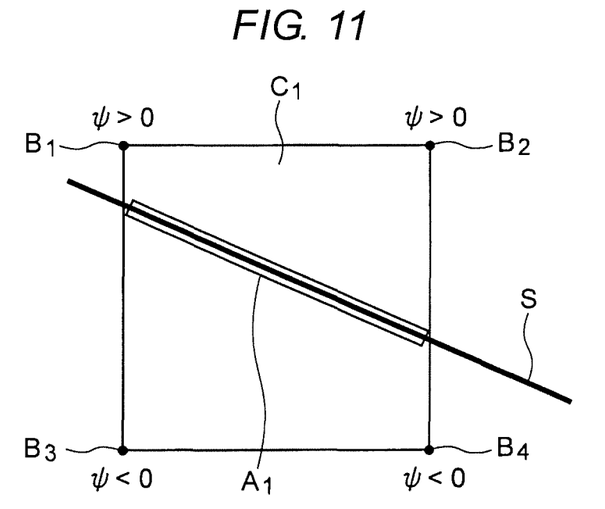
FIG. 11 is a schematic diagram illustrating a topography simulation method of some embodiments.

FIG. 11 is a schematic diagram illustrating a topography simulation method of some embodiments.

FIG. 11 illustrates a cell $C_1$, a surface segment $A_1$ in the cell $C_1$, and lattice points $B_1$ to $B_4$ constituting the vertices of the cell $C_1$. In some embodiments, since the lattice points $B_1$ and $B_2$ are located outside of the material, the values of the level set function $\psi$ at the lattice points $B_1$ and $B_2$ are positive ($\psi>0$). In some embodiments, since the lattice points $B_3$ and $B_4$ are located inside of the material, the values of the level set function $\psi$ at the lattice points $B_3$ and $B_4$ are negative ($\psi<0$). Thus, in some embodiments, if the cell $C_1$ is located at the material surface S, the values of the level set function $\psi$ at the lattice points $B_1$ to $B_4$ constituting the cell $C_1$ may have both positive and negative values.

Figure 12:
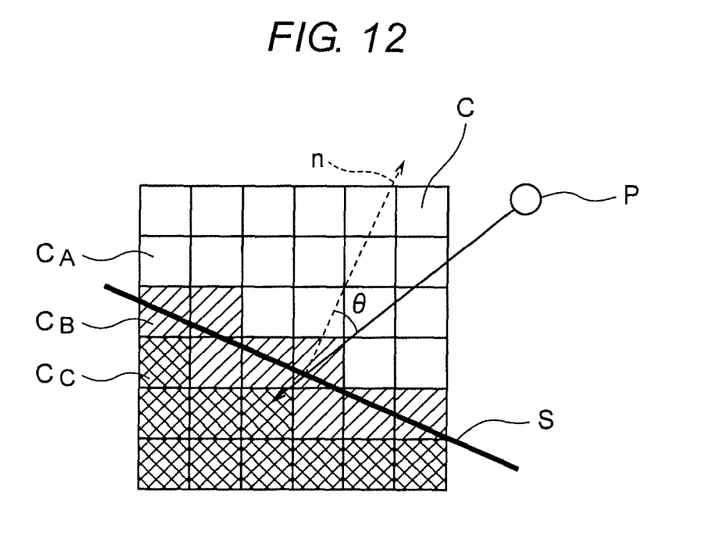
FIG. 12 is a schematic diagram illustrating the topography simulation method of some embodiments.

FIG. 12 is a schematic diagram illustrating the topography simulation method of some embodiments.

FIG. 12 illustrates a particle P which is incident on the material surface S. A reference symbol n indicates a normal vector of the material surface S. A reference symbol θ indicates an angle between the direction of motion of the particle P and the normal vector n. FIG. 12 further depicts a space cell $C_A$ which is located in the outside of the material, a surface cell $C_B$ which is located in the material surface S, and an internal cell $C_C$ which is located in the interior of the material. In some embodiments, in each lattice point constituting the space cell $C_A$, the value of the level set function θ is positive. In some embodiments, in each lattice point constituting the internal cell $C_C$, the value of the level set function $\psi$ is negative.

Here, a description will be given on step S14 (see FIG. 6), with reference to FIG. 11 and FIG. 12. The cell $C_1$ of FIG. 11 corresponds to the surface cell $C_B$. In some embodiments (e.g., those illustrated in FIG. 1-FIG. 10), determination as to whether or not the particle P collides with the cell $C_1$ is performed based on whether or not the trajectory of the particle P intersects the surface segment $A_1$ in the cell $C_1$ (step S14). Meanwhile, in some embodiments, determination as to whether or not the particle P collides with the cell $C_1$ is performed, based on the values of the level set function $\psi$ at the lattice points $B_1$ to $B_4$ constituting the cell $C_1$, and the values of the level set function $\psi$ at the lattice points constituting the surface cell $C_B$ other than cell $C_1$ (step S14). According to some embodiments, since the collision determination is performed with the calculation of the position of the surface segment $A_1$ being omitted, it is possible to speed up the calculation of the collision determination which is performed frequently.

Figure 13:
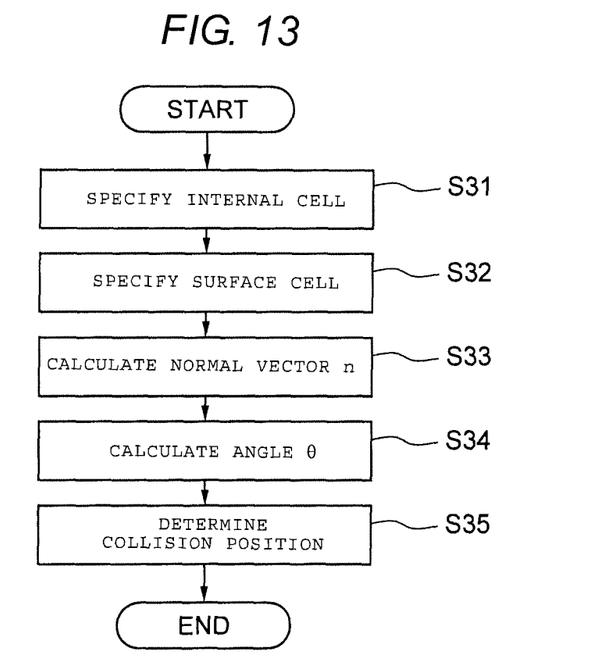
FIG. 13 is a flowchart illustrating the topography simulation method of some embodiments.

FIG. 13 is a flowchart illustrating the topography simulation method of some embodiments. FIG. 13 illustrates the flow of step S14 in some embodiments.

First, in some embodiments, the trajectory of the particle is calculated, and the type of each cell on the trajectory is specified. In some embodiments, if ψ at all lattice points constituting a certain cell is positive, the cell is a space cell (e.g., the cell $C_A$ in FIG. 12). In some embodiments, if ψ at all lattice points constituting a certain cell is negative, the cell is an internal cell (e.g., the cell $C_C$ in FIG. 12). In some embodiments, if ψ at lattice points constituting a certain cell includes 0, or positive and negative values, the cell is a surface cell (e.g., the cell $C_B$ in FIG. 12). As a result, for example, the internal cell $C_C$ to which a particle is first input is specified (step S31). In some embodiments, a particle collides with the material surface S, at any of the surface cells $C_B$ through which the particle passes, before reaching the internal cell $C_C$.

Thus, in some embodiments, after the internal cell $C_C$ to which a particle is first input is specified, a surface cell $C_B$ through which the particle passes last before reaching the internal cell CC is specified (step S32). In some embodiments, the center of the internal cell $C_C$ that is specified in step S31 and the material surface S are considered to be separated by a distance of about a cell size on average. In some embodiments, the average movement distance of the particle from the collision position to the internal cell $C_C$ is given by cell size/cos θ. Thus, in some embodiments, the particles is considered to collide with the material surface S, at the surface cell $C_B$ which is away from the internal cell $C_C$ on the trajectory by cell size/cos θ. Therefore, in some embodiments, the collision position is specified by using the value of cell size/cos θ.

In some embodiments, a normal vector n in the surface cell $C_B$ which is specified in step S32, and the angle θ is calculated from the normal vector n (steps S33 and S34). In some embodiments, the normal vector n in the surface cell $C_B$ can be calculated from the values of the level set function ψ at the lattice points constituting the surface cell $C_B$. For example, when the surface cell $C_B$ is a cell C1 of FIG. 11, the normal vector n can be calculated from the values of the level set function ψ at the lattice points B1 to B4 constituting the cell C1.

Next, in some embodiments, the position of the particle is returned from the internal cell $C_C$ which is specified in step S31 on the trajectory by a distance of cell size/cos θ. In some embodiments, if the cell at this position is the surface cell $C_B$, it is determined that the surface cell $C_B$ is at the collision position. In some embodiments, the surface cell $C_B$ may be the same as the surface cell $C_B$ specified in step S32. In some embodiments, the surface cell $C_B$ may be different from the surface cell $C_B$ specified in step S32. Meanwhile, in some embodiments, if the cell at this position is the space cell $C_A$, the surface cell $C_B$ that the particle first reaches after passing through the space cell $C_A$ is determined to be the collision position. In this way, the collision position of the particle is determined (step S35 in FIG. 13).

As described above, in some embodiments, the internal cell $C_C$ on which the particle is first incident is specified, the surface cell $C_B$ which the particle passes the last before reaching the internal cell $C_C$ is specified, and the cell at the collision position of the particle is specified based on the value of the level set function ψ at the lattice points constituting the surface cell $C_B$. In some embodiments, the normal vector n is calculated from the value of the level set function ψ, the angle θ is calculated from the normal vector n, and the cell at the collision position is specified based on the value of cell size/cos θ. Therefore, according to some embodiments, since collision determination is performed by omitting calculation for surface segments, it is possible to speed up the calculation of the collision determination.

Figure 14A:
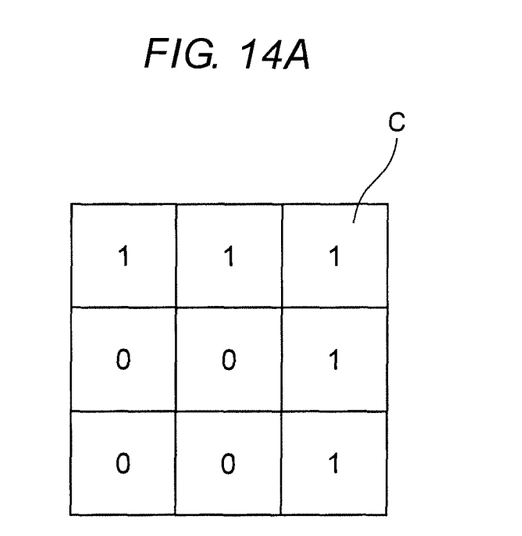
FIG. 14A and FIG. 14b are schematic diagrams illustrating a topography simulation method of some embodiments.
Figure 14B:
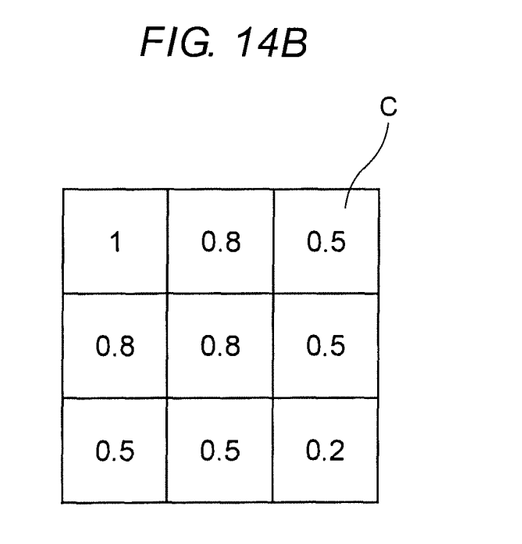

FIG. 14A and FIG. 14B are schematic diagrams illustrating a topography simulation method of some embodiments.

The cell C in some embodiments is capable of holding characteristic information indicating the characteristics of material in the cell C. For example, each cell C in FIG. 14A has a value of 0 or 1 as an identifier indicating the type of the material in each cell C. In some embodiments, the value 0 may indicate that the material is silicon. In some embodiments, the value 1 may indicate that the material is silicon oxide. Such an identifier is used, for example, when performing topography simulation in the oxidation reaction of silicon.

The topography simulation of some embodiments is performed using the characteristic information that the cell C has. For example, in some embodiments, if oxygen molecules collide with a certain cell C, it is determined based on the identifier of this cell C whether or not the topography of this cell C changes (step S15 of FIG. 6). At this time, in some embodiments, if the identifier is 0 (silicon), it is determined that the topography of the cell C is changed, while the identifier is changed into 1 (silicon oxide) in response to the oxidation of silicon. As a result, in some embodiments, the values of the level set function at the lattice points constituting the cell C are updated (step S16 in FIG. 6). In some embodiments, when the identifier is 1 (e.g., silicon oxide), it is determined that the topography of the cell C is not changed. As a result, in some embodiments, the values of the level set function at the lattice points constituting the cell C are not updated (step S16 in FIG. 6). In this way, in some embodiments, the characteristic information that is held in the cell C affects the update of the value of the level set function.

In some embodiments, even when fluorine molecules collide with the cell C, it is determined whether or not the topography of the cell C is changed, based on the identifier of this cell C (step S15 of FIG. 6). At this time, in some embodiments, if the identifier is 1 (e.g., silicon oxide), it is determined that the topography of the cell C is changed, while the identifier is changed into 0 (e.g., silicon) in response to the reduction of the silicon oxide. As a result, the values of the level set function at the lattice points constituting the cell C are updated (step S16). In some embodiments, when the identifier is 0 (silicon), it is determined that the topography of the cell C is not changed. As a result, the values of the level set function at the lattice points constituting the cell C are not updated (step S16).

In some embodiments, in the example of FIG. 14A, it is assumed that each cell C includes one of silicon and silicon oxide, and it is not assumed that each cell C includes both silicon and silicon oxide. In some embodiments, if it is assumed that each cell C includes both silicon and silicon oxide, the coverage of each cell C is introduced. For example, when the coverage of a certain cell C is 30%, the cell C includes silicon 30% and silicon oxide 70%. In the example of FIG. 14A, it is possible to output the final topography of the same accuracy as in the case of introducing coverage by performing topography simulation for simulating a relatively long time of process.

Further, in some embodiments, each cell C of FIG. 14B has a value of 0 to 1, as an identifier indicating the composition of the material in each cell C. In some embodiments, this value indicates the composition ratio of silicon in the $Si_xN_{1-x}$ (e.g., silicon nitride). In some embodiments, such an identifier is used when performing topography simulation, for example, in the deposition reaction of silicon nitride.

In this way, in some embodiments, when representing the characteristic information of each cell C as a numeric value, there may be a small number of types of numeric values as in FIG. 14A, or a large number of types of numeric values as in FIG. 14B. For example, if the type of material in the cell C is handled with the values of FIG. 14A, there is an advantage that the Langmuir type of surface reaction can be readily handled with consideration of equilibrium of adsorption and desorption. Further, in some embodiments, if the property of material in the cell C is handled with the values in FIG. 14B, there is an advantage that it is possible to accurately handle materials having complex properties.

FIG. 15 is an external view illustrating a configuration of a topography simulation apparatus of some embodiments.

The topography simulation apparatus of FIG. 15 includes a control unit 11, a display unit 12, and an input unit 13.

The control unit 11 is a device that controls the operation of the topography simulation apparatus. The control unit 11 performs, for example, the topography simulation method of some embodiments (e.g., those illustrated in FIG. 1 to FIG. 14B).

The display unit 12 is provided with a display device such as a liquid crystal monitor. For example, the display unit 12 displays an input screen of the setting information of topography simulation, and an output screen of a calculation result of the topography simulation.

The input unit 13 is provided with an input device such as a keyboard 13a and a mouse 13b. For example, the input unit 13 is used for input of the setting information of the topography simulation.

FIG. 16 is a block diagram illustrating a configuration of the control unit 11 of FIG. 15.

The control unit 11 includes a processor (e.g., central processing unit (CPU)) 21, a read only memory (ROM) 22, a random access memory (RAM) 23, a hard disk drive (HDD) 24, a memory drive 25 such as a compact disc (CD) drive and a digital versatile disk (DVD) drive, and a memory interface (I/F) 26 such as a memory port and a memory slot.

In some embodiments, a topography simulation program for executing the topography simulation methods is stored in the ROM 22 or the HDD 24. When a predetermined instruction is input from the input unit 13, the CPU 21 reads the topography simulation program from the ROM 22 or the HDD 24, develops the read program to the RAM 23, and performs topography simulation by using this program. Various pieces of data generated during the process are stored in the RAM 23.

It should be noted that, in some embodiments, a computer-readable recording medium which non-temporarily records the topography simulation program is prepared, and the topography simulation program is installed in the ROM 22 or the HDD 24 from the recording medium. An example of such a recording medium is a CD-ROM or a DVD-ROM.

In addition, in some embodiments, the topography simulation program may be downloaded through a network such as the Internet, and installed in the ROM 22 or the HDD 24.

As described above, according to some embodiments, it is possible to provide a topography simulation apparatus and a topography simulation program for executing the topography simulation method.

While certain embodiments have been described, these embodiments have been presented by way of example only, and are not intended to limit the scope of the present disclosure. Indeed, the embodiments described herein may be embodied in a variety of other forms; furthermore, various omissions, substitutions and changes in the form of the embodiments described herein may be made without departing from the spirit of the present disclosure. The accompanying claims and their equivalents are intended to cover such forms or modifications as would fall within the scope and spirit of the present disclosure. Moreover, some or all of the above-described embodiments can be combined when implemented.

What is claimed is:

1. A topography simulation apparatus comprising a processor and a memory connected to the processor, the memory storing instructions executable by the processor to:
   set a function indicating a position relationship between a point in a calculation region and a material surface in the calculation region;
   determine whether or not a particle moving in the calculation region collides with the material surface, wherein the particle simulates a molecule or an ion; and
   update a value of the function, responsive to determining that the particle collides with the material surface.

2. The apparatus according to claim 1,
   wherein the memory further stores instructions executable by the processor to determine whether or not a topography of the material surface changes due to the particle, responsive to determining that the particle collides with the material surface,
   wherein the instructions to update the value of the function include instructions executable by the processor to update the value of the function, responsive to determining that the particle collides with the material surface and the topography of the material surface changes due to the particle.

3. The apparatus according to claim 1,
   wherein the instructions to determine whether or not the particle moving in the calculation region collides with the material surface include instructions executable by the processor to calculate a trajectory of the particle by a direct simulation Monte Carlo (DSMC) method.

4. The apparatus according to claim 1,
   wherein the instructions to update the value of the function include instructions executable by the processor to update the value of the function such that a surface moving distance of the material each time the particle collides is constant.

5. The apparatus according to claim 1,
   wherein the calculation region includes a plurality of cells obtained by dividing the calculation region, and a plurality of lattice points constituting each cell.

6. The apparatus according to claim 5,
   wherein the instructions to determine whether or not the particle moving in the calculation region collides with the material surface include instructions executable by the processor to specify a cell which is located in a collision position of the particle, and
   wherein the instructions to update the value of the function include instructions executable by the processor to update the value of the function at lattice points constituting the cell which is located in the collision position of the particle.

7. The apparatus according to claim 6,
   wherein the instructions to determine whether or not the particle moving in the calculation region collides with the material surface include instructions executable by the processor to specify the cell which is located in the collision position of the particle, based on values of the function at lattice points constituting a cell which is located in the material surface.

8. The apparatus according to claim 5,
wherein each cell has characteristic information indicating characteristics of a material in the cell, and
wherein the instructions to update the value of the function include instructions executable by the processor to update the value of the function, based on the characteristic information.

9. A non-transitory computer-readable storage medium storing instructions as a topography simulation program executable by a processor to:
set a function indicating a position relationship between a point in a calculation region and a material surface in the calculation region;
determine whether or not a particle moving in the calculation region collides with the material surface wherein the particle simulates a molecule or an ion; and
update a value of the function, responsive to determining that the particle collides with the material surface.

10. The non-transitory computer-readable storage medium according to claim 9,
wherein the medium further stores instructions executable by the processor to determine whether or not a topography of the material surface changes due to the particle, responsive to determining that the particle collides with the material surface,
wherein the instructions to update the value of the function include instructions executable by the processor to update the value of the function, responsive to determining that the particle collides with the material surface and the topography of the material surface changes due to the particle.

11. The non-transitory computer-readable storage medium according to claim 9,
wherein the instructions to determine whether or not the particle moving in the calculation region collides with the material surface include instructions executable by the processor to calculate a trajectory of the particle by a direct simulation Monte Carlo (DSMC) method.

12. The non-transitory computer-readable storage medium according to claim 9,
wherein the instructions to update the value of the function include instructions executable by the processor to update the value of the function such that a surface moving distance of the material each time the particle collides is constant.

13. The non-transitory computer-readable storage medium according to claim 9,
wherein the calculation region includes a plurality of cells obtained by dividing the calculation region, and a plurality of lattice points constituting each cell.

14. The non-transitory computer-readable storage medium according to claim 13,
wherein the instructions to determine whether or not the particle moving in the calculation region collides with the material surface include instructions executable by the processor to specify a cell which is located in a collision position of the particle, and
wherein the instructions to update the value of the function include instructions executable by the processor to update the value of the function at lattice points constituting the cell which is located in the collision position of the particle.

15. A topography simulation method comprising:
setting a function indicating a position relationship between a point in a calculation region and a material surface in the calculation region;
determining that a particle moving in the calculation region collides with the material surface, wherein the particle simulates a molecule or an ion;
updating a value of the function, responsive to determining that the particle collides with the material surface; and
outputting a changed topography of the material surface based on the updated value of the function.

16. The method according to claim 15, wherein the calculation region includes a plurality of cells obtained by dividing the calculation region, and a plurality of lattice points constituting each cell.

17. The method according to claim 16,
wherein the determining that the particle moving in the calculation region collides with the material surface includes specifying a cell which is located in a collision position of the particle, and
wherein the updating the value of the function includes updating the value of the function at lattice points constituting the cell which is located in the collision position of the particle.

18. The method according to claim 16,
wherein each cell has characteristic information indicating characteristics of a material in the cell, and
wherein the updating the value of the function includes updating the value of the function, based on the characteristic information.

* * * * *